United States Patent [19]

Tsang

[11] Patent Number: 4,683,092

[45] Date of Patent: Jul. 28, 1987

[54] CAPSULE LOADING TECHNIQUE

[75] Inventor: Wen-Ghih Tsang, Lexington, Mass.

[73] Assignee: Damon Biotech, Inc., Needham Heights, Mass.

[21] Appl. No.: 752,384

[22] Filed: Jul. 3, 1985

[51] Int. Cl.$^4$ .......................... A61K 9/36; A61K 9/38; A61K 9/52; B01J 13/02

[52] U.S. Cl. ..................................... 264/4.3; 210/650; 424/455; 424/491; 424/493; 428/402.2; 514/962; 604/891

[58] Field of Search ....................... 264/4.3; 428/402.2; 424/34, 36, 35; 514/962

[56] References Cited

U.S. PATENT DOCUMENTS

| | | | |
|---|---|---|---|
| 3,516,942 | 6/1970 | Scarpelli | 252/316 |
| 3,516,943 | 6/1970 | Brynko et al. | 252/316 |
| 3,639,036 | 2/1972 | Sternberg et al. | 260/2.5 B |
| 3,657,143 | 4/1972 | Crainich | 252/316 |
| 3,657,144 | 4/1972 | Yoshida | 252/316 |
| 3,664,963 | 5/1972 | Pasin | 252/316 |
| 3,780,195 | 12/1973 | Balassa | 426/350 |
| 4,272,398 | 6/1981 | Jaffe | 252/316 |
| 4,324,683 | 4/1983 | Lim | 252/316 |
| 4,389,330 | 6/1983 | Tice et al. | 427/213 |
| 4,389,419 | 6/1983 | Lim et al. | 426/72 |
| 4,391,909 | 7/1983 | Lim | 424/35 X |
| 4,492,720 | 1/1985 | Mosier | 427/213 |
| 4,508,703 | 4/1985 | Redziniak et al. | 424/38 |
| 4,515,736 | 5/1985 | Deamer | 264/4.3 |

FOREIGN PATENT DOCUMENTS 0126537 4/1984 European Pat. Off. .

Primary Examiner—Richard D. Lovering
Attorney, Agent, or Firm—Lahive & Cockfield

[57] ABSTRACT

Disclosed is a method for loading capsules having a semipermeable membrane with a chemically active substance to be released over time. The method first involves gradually deflating and dehydrating the capsules and subsequently soaking the deflated capsules in a solution containing the substance to be encapsulated. After loading, the permeability of the capsule may be adjusted to accommodate the requirements of the end use. The loaded capsules of this invention may be used in a variety of applications, including use as a bioimplantable drug or biochemical delivery system.

23 Claims, No Drawings

CAPSULE LOADING TECHNIQUE

BACKGROUND OF THE INVENTION

1. Field of the Invention

This invention relates to microcapsules. More particularly, this invention relates to (i) techniques for loading substances into microcapsules to create an intracapsular reservoir of the substance which is releaseable from the microcapsule at a substantially constant rate over a period of time, and (ii) techniques for using microcapsules as separation and filtration devices.

2. Prior Art

The use of microcapsules containing an intracapsular volume of a substance such as medicinal compounds, biochemical compounds, insecticides, fragrances, and other chemically active substances capable of being released over a period of time is well known. Such compositions are of particular importance in the field of medicine as they have potential for use as bioimplantable or ingestable drug delivery systems.

A critical step in the preparation of such microcapsules is that of loading the capsules with the substance to be released. This step is often quite costly and time consuming. The greatest expense in loading these microcapsules is often incurred as a result of inefficient loading of the substance. In most loading techniques, a relatively large quantity of the substance is needed to load the microcapsules while only a small portion of this substance may actually be loaded, and the remainder may sometimes have to be discarded or further processed before reuse. It is important to avoid waste and inefficient loading of the substance as the substances are often quite expensive.

There are several techniques for the loading of microcapsules with chemically active substances. Perhaps the most common of these techniques is that of liquid-liquid phase separation as disclosed in U.S. Pat. Nos. 3,657,144; 3,664,963; 3,780,195; 4,272,398; and 4,389,330. This technique involves the simultaneous preparation and loading of the capsules. Generally, a substance to be encapsulated and a membrane-forming material are dissolved in a solvent. Next, the solvent, having dissolved substance and membrane-forming material is dispersed in a continuous-phase medium. A portion of the solvent is subsequently evaporated and microcapsules are formed as the membrane-forming material leaves solution and envelopes the substance. Finally the remainder of the solvent is extracted.

Another capsule loading technique is that described by Lim in pending U.S. patent application Ser. No. 485,471, now abandoned. Lim forms capsules having selectively permeable hydrogel membranes which define an aqueous intracapsular volume. These capsules are suspended in a concentrated solution of a substance to be encapsulated within the capsules. The concentration gradient across the membrane causes the substance to diffuse through the membrane. It is generally necessary to soak the capsules one or more times for several hours each time.

U.S. Pat. No. 4,515,736 describes a technique for loading liposomes.

The known capsule loading techniques produce adequate loaded capsules, capable of many end uses. However, the loading process could be substantially shortened and performed less expensively by other techniques. Moreover, it would be useful to develop a loading technique whereby the blank capsules could be conveniently stored and subsequently loaded.

SUMMARY OF THE INVENTION

Accordingly, it is an object of this invention to provide a capsule which is easily and rapidly loaded with a substance to be released over a period of time.

A further object of this invention is to provide a method for dehydrating semipermeable capsules such that the capsule membrane remains intact after dehydration and the resulting dehydrated capsules may be stored and later reconstituted.

Another object is to provide a method of loading dehydrated capsules with a substance to be released over time.

Yet another object of this invention is to provide a method of using microcapsules as filtration and concentration devices.

Finally, it is an object of this invention to provide easily loaded, biocompatible capsules containing a substance which is to be released over a period of time, preferably at a substantially constant rate.

Other objects and features of this invention will be apparent from the following disclosure.

In one aspect, the present invention comprises a method for obtaining a composition of deflated, dehydrated capsules with intact, selectively permeable membranes. The capsule membranes are expandable upon rehydration with an aqueous solution containing a substance, e.g., a chemically active substance, which is to be encapsulated within the capsules and released from the capsule over time.

Rehydration of the capsules is accomplished by soaking the capsules in a solution containing the chemically active substance. The solution diffuses through pores in the membrane to create a reservoir of the substance within the interior volume of the capsules. Depending upon the nature of the substance and the membrane pore size, the substance in the solution can be loaded non-selectively or selectively. Using a preferred embodiment of the invention, after the capsules have been loaded, the permeability of the membrane may be adjusted, e.g., by applying a polymer overcoating thereto. Alternatively, the loading solution may itself contain a polymer which overcoats the membrane to adjust the capsule permeability.

In another aspect, the invention provides a method of treating hydrated capsules having a semipermeable hydrogel membrane to obtain deflated, dehydrated capsules with an intact, expandable membrane This technique involves gradually dehydrating the capsules with successive washes in a solution containing increasing concentrations of a dehydrating agent. The dehydrating agents of this invention may be organic solvents (e.g., ethanol, methanol, acetone, ethers or esters) or a high osmotic pressure aqueous solution (e.g., concentrated salt or sugar solutions). The preferred dehydrating agent is, however, ethanol. The dehydrating agent extracts fluids from the intracapsular volume and the membrane of the capsule, causing the capsule to shrink or deflate. Eventually, a substantially fully dehydrated, flake-like, "crenated" capsule is obtained. Any remaining organic solvent or aqueous solution may be removed by vacuum drying. The resultant dehydrated capsule may be stored indefinitely, and is expandable upon contact with an aqueous solution.

The loaded microcapsules of this invention are useful in a variety of applications. For example, they may be loaded with a drug, a hormone, a vitamin, or another physiologically active substance for implantation by injection or other means within the body of an animal host. The loaded substance may be released over a period of time. It is possible to regulate the release rate of a composition of microcapsules to accommodate the needs of a specific end use.

It is believed that the invention disclosed herein is most useful in the medical field as a drug delivery system. For example, deflated microcapsules may be packaged and stored. A physician who desires a patient to receive a given quantity of medication or other such compound over a given period of time may simply obtain the deflated microcapsules designed for a specific release rate and load the capsules as described herein. The loaded capsules may then be injected or orally administered, and the substance will be released over a substantial period of time.

The microcapsules of this invention have also been found to be useful in filtration or separation applications. The deflated capsules may be added to a solution containing a variety of molecules with varying molecular weights. Those particles having a lower, predetermined molecular weight range, for example, will permeate the capsule membrane and reconstitute the capsules while the larger particles will remain in the solution. The selectively loaded capsules may then be recovered, and, if desired, the substance loaded within the capsules may also be recovered.

DETAILED DESCRIPTION OF THE INVENTION

As noted above, in the present invention previously prepared porous capsules are dehydrated to form deflated capsules. The deflated capsules have been shrunk as a result of the extraction of fluids from their membranes and interior volumes such that they take on the appearance of a coarse, powdery substance. The deflated capsules may be stored and subsequently loaded with a substance to be released over time. Loading of the capsules is accomplished by adding a quantity of the deflated capsules to a solution containing the substance to be loaded. Within a short period of time the substance will diffuse through the membrane to establish an intracapsular reservoir and will thereby reconstitute the capsule. The substance contained within the intracapsular volume is releaseable from the capsule over a period of time. The release rate of the substance is determined by the permeability of the capsule membrane and hence may be regulated by controlling membrane pore size and the membrane thickness during fabrication of the capsules before dehydration, or by applying a polymeric overcoating to the capsules during or after loading.

Capsules deflated and dehydrated according to the present invention may be prepared by the method disclosed by Tsang et al. in pending U.S. patent application Ser. No. 579,494, or by Lim in U.S. Pat. No. 4,324,683, the disclosures of which are incorporated herein by reference.

Generally, the capsules disclosed by Tsang are formed by gelling a water soluble polyanionic polymer, for example an acidic polysaccharide, which may or may not contain a material to be encapsulated within the capsule, to form hydrated discrete gelled masses. The gelled masses are expanded with an aqueous solution to become further hydrated. One or more membrane layers comprising a polycationic polymer such as polyvinyl amines, aminated polysaccharides, polyaminated polypeptides, their salts or mixtures thereof, is bonded to the anionic polymer through a reaction between the cationic groups of the polycationic polymer and the anionic groups on the anionic material. Optionally, the capsule may be post-coated with a polyanionic polymer layer.

The preferred material for the polyanionic polymer is a polycarboxylated polymer such as algin. The preferred polycationic polymer is a polyaminated polymer such as polylysine, polyglutamine, or polyornithine.

It is to be understood that in the present disclosure the capsules of this invention are, from time to time, alternatively termed "capsules" or "microcapsules". These terms are used interchangeably as it is believed that the present invention is applicable to capsules of virtually all sizes. However, in the preferred embodiment the capsules of this invention range in size from a few microns to several millimeters.

The deflated microcapsule composition may be prepared by gradually dehydrating the microcapsules. The dehydration method of this invention yields shrunken, or deflated, microcapsules which are flake-like in appearance and which have intact membranes. The membranes of these microcapsules are readily expandable upon being exposed to an aqueous solution.

In the preferred embodiment, the capsules are dehydrated by washing the capsule composition with increasingly concentrated solutions containing a dehydrating agent such as an organic solvent or a high osmotic pressure aqueous solution. The preferred organic solvent is ethanol while the preferred high osmotic pressure solution is a concentrated saline solution.

For example, the capsule composition is preferably initially washed with an organic solvent, such as a 25% ethanol solution. After agitating the mixture for approximately 3 minutes, the supernatant is then discarded, leaving only the intact microcapsules. This procedure is repeated using ethanol solutions with concentrations of 25%, 50%, 75% and 100%. The washing with 100% ethanol is repeated approximately three times. Following the final wash, the deflated microcapsules are recovered by any suitable technique. One preferred technique is that of vacuum filtration using filter paper or a sintered glass filter. After recovery, the deflated capsules are dried and may then be stored or immediately loaded.

While the above dehydration procedure is that which is preferred, it is possible to use fewer washes and different concentrations of dehydrating solutions. However, it has been found that rapid dehydration using, for example, a single wash with a 100% ethanol solution causes the salts of the capsule solution to precipitate resulting in a less uniform and less desirable membrane.

Generally, each wash should contain approximately 2-3 ml dehydrating solution per milliliter of hydrated capsules. Also, the duration of each wash should be approximately 3 minutes.

The gradual dehydration of the capsules has been found to be necessary to prevent the precipitation of salts within the membrane which would damage the integrity of the membrane.

Potentially, other semi-dehydration techniques which do not damage membrane integrity could be used. For example, dehydration could be accomplished using high osmotic pressure aqueous solutions such as concentrated salt or sugar solutions. Following the completion of this process the capsules are preserved in a partially dehydrated state. Upon contact with a less concentrated loading solution, the partially dehydrated capsule becomes rehydrated to approximately 290 mosm/kg.

The deflated capsules dehydrated with an organic solvent are generally recovered using vacuum filtration. After isolating the deflated capsules, the vacuum chamber is purged with a gas. If air is used as a purge gas or if the deflated capsules are stored in air, a minute air bubble will form upon reloading the capsule. This bubble will solubilize in approximately five hours. In applications where the loaded microcapsules must not contain a gas bubble, a highly water soluble gas such as $CO_2$ should be used as a purge gas. The use of $CO_2$ in this manner will prevent the formation of a gas bubble. In addition, deflated capsules should be stored in a $CO_2$ environment following recovery to ensure that gas bubbles are not formed during the reloading step.

The deflated, permeable capsules are loaded with one or more chemically active substances by simply adding a quantity of the deflated microcapsules to a quantity of solution containing the substance. Due to the concentration gradient across the membrane, the substance will flow from the concentrated extracapsular volume, through the pores and into the less concentrated intracapsular volume to establish a reservoir of the substance within the capsule. Eventually, the capsule will be fully expanded and the concentration inside the capsule will be substantially equal to the concentration outside the capsule.

The osmotic pressure within the capsule after loading is preferably the same or greater than the osmotic pressure within the capsule before dehydration.

Preferably, however, a quantity of deflated capsules sufficient to fully absorb the loading solution is added to a predetermined volume of solution containing the substance or substances to be encapsulated. In this embodiment the deflated capsules will act as sponges and the solution will pass through the membrane to expand the capsules. Diffusion will continue until the capsules are fully expanded and the supply of solution is depleted.

It has been discovered that the amount of substance which will fully load or hydrate the capsules can generally be determined by placing hydrated capsules (i.e. capsules not yet dehydrated) in close packed relation in solution in a graduated cylinder or similar calibrated receptacle. The volume of liquid which the capsules will hold (real capsule volume) is determined generally by the following relationship:

real capsule volume = total volume/1.35, where the total volume is the total volume of liquid and microcapsules contained in the calibrated receptacle. This loading technique results in a significant cost savings as there is essentially no waste of the chemically active substance. It is especially useful where a scarce or expensive substance is to be encapsulated.

The time required for loading the capsules with a substance naturally will depend upon many factors, such as the molecular weight of the material to be added and the membrane pore size. Generally, the greater the molecular weight of the material to be loaded and the smaller the membrane pore size, the greater the amount of time required for loading the capsule. Nevertheless, the loading method described herein is considerably faster than known techniques and it may require as little as five minutes. Loading times for various substances will be discussed more fully in the Examples.

The loading solution generally comprises a solvent in which the capsules are not soluble, for example water, and a dissolved or dispersed substance which is to be loaded into the capsules and released over a period of time. The concentration of a substance to be added is entirely dependent upon the requirements of the end use. However, in the present invention the concentration of the intracapsular volume may be substantially equal to that of the loading solution.

The substances which may be encapsulated in accordance with the invention to produce compositions characterized by substantially constant, sustained release can vary widely. The only limiting factors appear to be that it is difficult to produce a membrane that will be the dominating factor in controlling the diffusion rate in the case of very low molecular weight materials, e.g., 200 daltons or below. Also, capsule membranes uniformly permeable to substances having a molecular weight greater than about $10^6$ daltons are difficult to synthesize.

Nonlimiting examples of substances which may be loaded into the capsules for sustained release include hormones, antibodies, antigens, enzymes, lymphokines, vaccines, natural or synthetic drugs, fertilizer, pesticides, fungicides, plant hormones and growth factors, flavors, perfumes, preservatives, and nutrients such as cell-culture nutrients.

After the microcapsules have been loaded with the desired substance, the permeability of the membrane optionally may be adjusted. Various methods for the control of membrane porosity are disclosed in pending U.S. patent application Ser. No. 485,471, now abandoned, which is incorporated herein by reference. In the preferred embodiment, a polycationic polymer may be used to overcoat the capsule membrane after loading to control the permeability. The effect any given overcoating has on limiting permeability depends on such factors as the molecular weight of the overcoating material, the amount of overcoating material used, and the duration of the overcoating process.

The overcoating polymers preferred in the present invention are polylysine, polyornithine, poly-$\alpha$, $\gamma$-diaminobutanoic acid, poly-$\alpha,\beta$-diaminopropionic acid, polyvinylamine, and various copolymers or mixtures thereof. Generally, the overcoating polymers may be ranked as follows in terms of ability to decrease the release rate, with the first polymer most significantly decreasing the release rate: poly-$\alpha,\gamma$-diaminobutanoic acid; poly-$\alpha,\beta$-diaminopropionic acid; polyvinylamine; polyornithine; polylysine.

From the foregoing, it should be apparent that some experimentation will be required in the design of a specific composition for dispensing a given substance. However, in view of this disclosure, those skilled in the art will be able to produce a variety of specific compositions having a desired rate of release. In some cases it is difficult to set a constant release rate of a given microcapsule at a specific desired level. However, it is relatively simple to control the average rate of release of a large number of capsules at an arbitrary value. Thus, dosage, for example, can be controlled by supplying a number of capsules which together release the desired quantity of the substance to be dispensed at a constant rate over a significant time.

In another embodiment, the overcoating polymer may be incorporated into the loading solution so that the permeability of the capsule will be fixed simultaneously with the loading of the capsule.

If the substance contained within the capsule is at a concentration in excess of the desired extracapsular concentration, and the porosity of the membrane is such that molecules passing therethrough are hindered, molecules of the substance are released into the extracapsular environment at a substantially constant rate until the intracapsular concentration drops to a level where the intracapsular osmotic pressure is insufficient to support the membrane dependent transfer rate. The loaded capsules of this invention may thus be used in an environment which depletes the substance, e.g., by chemical modification, sorption, metabolic breakdown, ingestion, diffusion, or simple removal by fluid flow, to achieve a substantially constant rate of release.

The intracapsular concentration of the substance to be dispensed should be quite high, typically at least two orders of magnitude greater than the desired extracapsular concentration, and more preferably at least three. Generally, the higher the intracapsular concentration, the longer the release rate can be sustained. If the capsules are placed in an environment with no mechanism for removing the substance, then eventually the intracapsular and extracapsular concentration will equalize. Thus, loaded capsules may be stored as a suspension in a volume of a compatible solvent containing a concentration of the substance substantially equal to or greater than the intracapsular concentration. In this circumstance, net flow of the substance out of the capsules is prevented.

In a preferred embodiment, the hydrogel membranes of these capsules comprise a matrix of polymers ionically "cross-linked". These polymers are believed to define random intermolecular spaces which communicate with each other to form tortuous path pores through the membranes. It is believed that both the pore dimensions and the effective length of the pore across the membrane influence the kinetics of molecular diffusion. Molecules within the pores presumably undergo many random collisions, which, in the aggregate, ultimately determine the average time required for a molecule of a given dimension to traverse the membrane. Thus, the release rate of the encapsulated substance is determined by such factors as the pore size, pore configuration, and molecular weight of the substance. The release rate is of course expected to differ depending upon the end use of the loaded microcapsules.

The following non-limiting examples will further illustrate the processes of the invention and their advantages.

EXAMPLE 1

A sample of hydrated capsules previously prepared by known techniques is obtained. To this sample, a 25% ethanol solution is added in the amount of 2-3 ml ethanol per milliliter of hydrated capsules. The mixture is agitated for approximately three minutes and the ethanol solution is discarded. This procedure is repeated using ethanol concentrations of 25%, 50%, 75% and 100%. The wash with 100% ethanol solution is repeated three times. Following the final wash, the deflated capsules are recovered using vacuum filtration, and the vacuum chamber is purged with $CO_2$. The recovered capsules, which appear as a flake-like, coarse powdery material, are stored in a $CO_2$ environment.

EXAMPLE 2

The deflated capsules prepared as described in Example 1 are non-selectively loaded with bovine serum albumin (BSA) as follows. A 0.85% NaCl solution containing 3% BSA, by weight, is prepared. To this solution, a quantity of deflated capsules is added. Within approximately five minutes, the capsules are fully loaded with the loading solution. The loaded capsules are stored by suspending them in a solution of at least 3% BSA in 0.85% NaCl.

EXAMPLE 3

A 0.85% NaCl solution is prepared and to this is added 1% myoglobin by weight. A quantity of capsules dehydrated by Example 1 are added to this solution and within approximately five minutes the capsules are fully loaded. These loaded capsules are stored by suspending them in a solution of at least 1% myoglobin in 0.85% NaCl.

EXAMPLE 4

A soution of calf serum is obtained. Deflated capsules preppred by Example 1 are selectively loaded with smaller molecules contained within the calf serum by adding a quantity of the deflated capsules to the serum and allowing the molecules to diffuse through the capsule membrane. Within approximately 8 hours, the capsules are loaded with molecules of the calf serum having molecular weights ranging approximately from 90,000-100,000 daltons and below.

EXAMPLE 5

Capsules loaded according to Example 2, and not overcoated, were placed in a phosphate buffered saline solution (PBS) in the proportion of 10 parts PBS to 1 part capsules and the BSA was allowed to be released. The release rate approximated first order kinetics. The intracapsular concentration of BSA in the capsules was approximately 10 mg/ml at t=0. At t=360 hours the intracapsular concentration of BSA in the capsules was approximately 1.7 mg/ml. The time required for the intracapsular concentration to equal the extracapsular concentration ($t_½$) was approximately 48 hours.

EXAMPLE 6

Capiules loaded with BSA according to Example 2 were overcoated with polyornithine as follows A solution containing 1.5 mg/ml of polyornithine in a 0.85% saline solution was prepared. To this solution 1 ml of loaded capsules were added. This mixture was lightly agitated for approximately 30 minutes After overcoating with polyornithine, the capsules were recovered.

Using polyornithine overcoating techniques similar to that in Example 6, the release rate may be controlled to extend $t_½$ to beyond 360 hours.

What is claimed is:

1. A composition of matter comprising a previously formed, and deflated, dehydrated cpsule having an intact, selectively permeable membrane defining a substantially empty interior volume, said membrane being expandable upon rehydration with a solute and aqueous solution at a given concentration to produce a capsule containing said solution and capable of sustained release of said solute.

2. The composition of claim 1 wherein said membrane comprises a dehydrated hydrogel:

3. The composition of claim 1 wherein said membrane comprises a polycationic material bound to a polyanionic material.

4. The composition of claim 1 wherein said membrane comprises a polycarboxylated polymer bonded to a polyaminated polymer.

5. A method of producing a capsule containing a solute which is released therefrom over time, said method comprising the step of loading a plurality of deflated, dehydrated capsules of claim 1 with said solute by soaking said capsules in said solution to diffuse the solution into said interior volume, thereby to establish a reservoir of said solution therewithin, at substantially said given concentration.

6. The method of claim 5 comprising the additional step of treating said capsules after said loading step to decrease the permeability of said membrane.

7. A method of preparing a composition of deflated, dehydrated semipermeable capsules having intact membranes which define a substantially empty interior volume wherein said deflated, dehydrated, semipermeable capsules are capable of being reexpanded and rehydrated, said method comprising the step of dehydrating preformed capsules having hydrogel membranes by treating said preformed capsules with successive aqueous wash solutions having increasing concentrations of a dehydrating agent and thereafter removing residual dehydrating agent.

8. The method of claim 7 wherein said dehydrating agent is selected from the group consisting of organic solvents and high osmotic pressure aqueous solutions.

9. The method of claim 8 wherein said dehydrating agent is an ethanol solution.

10. A method of producing a sustained release composition, said method comprising the steps of:
   (a) providing preformed hydrated capsules each having a semipermeable, porous hydrogel membrane defining an intracapsular volume;
   (b) deflating and dehydrating said capsules with successive aqueous wash solutions having increasing concentrations of a dehydrating agent to obtain deflated, dehydrated capsules, each having intact, semipermeable membranes which define a substantially empty interior volume; and
   (c) loading said deflated, dehydrated capsules with a solute and aqueous solution by soaking the deflated, dehydrated capsules in the solute-containing aqueous solution to diffuse said solute into the intracapsular volume to yield a reconstituted, rehydrated capsule, having a reservoir of time-releasable solute.

11. The method of claim 10 further comprising the step of treating said capsules to adjust the permeability of the membrane.

12. The method of claim 11 wherein the membrane permeability is adjusted by decreasing the dimensions of said pores.

13. The method of claim 11 wherein the membrane permeability is adjusted by treating said capsules with a polymeric coating after loading said capsules.

14. The method of claim 11 wherein said hydrogel membrane comprises a polycationic material bound to polyanionic material.

15. The method of claim 14 wherein said polycationic polymer is selected from the group consisting of proteins comprising plural reactive nitrogen-containing cationic groups, polypeptides comprising plural reactive nitrogen-containing cationic groups, polyvinyl amines, salts thereof and mixtures thereof.

16. The method of claim 14 wherein said polycationic material is selected from the group consisting of polylysine, polyglutamine, and polyornithine.

17. The method of claim 14 wherein said polyanionic material is an acidic polysaccharide.

18. The method of claim 17 wherein said acidic polysaccharide is an algin.

19. The method of claim 11 wherein said hydrogel membrane comprises a polycarboxylated polymer bound to a polyaminated polymer.

20. The method of claim 11 wherein said dehydrating agent is selected from the group consisting of organic solvents and high osmotic pressure aqueous solutions.

21. The method of claim 11 wherein said dehydrating agent is an ethanol solution.

22. The method of claim 11 wherein said loading is accomplished by diffusion of solute through the pores of said membranes from a concentrated extracapsular volume to a less concentrated intracapsular volume, said loading continuing until the solute concentration of the intracapsular volume is substantially the same as the extracapsular volume.

23. The method of claim 11 wherein said loading is accomplished by diffusion of solute through the pores of said membranes from a concentrated extracapsular volume to a less concentrated intracapsular volume, said loading continuing until the extracapsular volume is fully absorbed by said capsules.

* * * * *